United States Patent
Nam et al.

(10) Patent No.: US 10,526,632 B2
(45) Date of Patent: Jan. 7, 2020

(54) METHOD FOR SELECTIVELY PRODUCING GINSENOSIDE F2, COMPOUND MC OR COMPOUND O FROM SAPONINS OF GINSENG BY ENZYMATIC PROCESS

(71) Applicant: AMOREPACIFIC CORPORATION, Seoul (KR)

(72) Inventors: Gi Baeg Nam, Yongin-si (KR); Dong Hyun Kim, Yongin-si (KR); Yong Deog Hong, Yongin-si (KR); Jun Seong Park, Yongin-si (KR); Kyoung Hee Byoun, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 15/769,964

(22) PCT Filed: Oct. 21, 2016

(86) PCT No.: PCT/KR2016/011900
§ 371 (c)(1),
(2) Date: Apr. 20, 2018

(87) PCT Pub. No.: WO2017/069561
PCT Pub. Date: Apr. 27, 2017

(65) Prior Publication Data
US 2018/0305726 A1    Oct. 25, 2018

(30) Foreign Application Priority Data

Oct. 22, 2015 (KR) .......................... 10-2015-0147353

(51) Int. Cl.
*C12P 33/00*    (2006.01)
(52) U.S. Cl.
CPC .................................. *C12P 33/00* (2013.01)
(58) Field of Classification Search
None
See application file for complete search history.

(56) References Cited

U.S. PATENT DOCUMENTS

| | | | | |
|---|---|---|---|---|
| 5,925,537 A * | 7/1999 | Sung | .................. | C07J 17/005 435/53 |
| 2006/0112495 A1* | 6/2006 | Rizzardi | .................. | D06L 4/12 8/115.51 |
| 2014/0357863 A1* | 12/2014 | Haldar | .................. | A61K 31/522 544/268 |

FOREIGN PATENT DOCUMENTS

| | | |
|---|---|---|
| KR | 2002-0058153 A | 7/2002 |
| KR | 10-2009-0061107 A | 6/2009 |
| KR | 10-2011-0123311 A | 11/2011 |
| KR | 10-2013-0003944 A | 1/2013 |

OTHER PUBLICATIONS

Translation of KR 1020060112257; published Nov. 30, 2006, downloaded from KIPO on Jun. 9, 2019 (Year: 2006).*
Sun et al. Anal. Methods (2015) 7: 4757-4762 (Year: 2015).*
Bae et al. Biol. Pharm. Bull. (2002) 25(6): 743-747 (Year: 2002).*
Sunwoo et al. Biotechnol. Lett. (2013) 35: 1017-1022 (Year: 2013).*
Sung-Ryong Ko et al., "Marked Production of Ginsenosides Rd, $F_2$, $Rg_3$, and Compound K by Enzymatic Method," Chem. Pharm. Bull., 2007, pp. 1522-1527, vol. 55, No. 10.
Hyun Jung Lee et al., "Utilization of hydrolytic enzymes for the extraction of ginsenosides from Korean ginseng leaves," Process Biochemistry, 2012, pp. 538-543, vol. 47.
International Search Report of PCT/KR2016/011900 dated Feb. 15, 2017.

* cited by examiner

*Primary Examiner* — Susan M Hanley
(74) *Attorney, Agent, or Firm* — Sughrue Mion, PLLC

(57) ABSTRACT

The present invention relates to a method for selectively producing ginsenoside F2, compound Mc or compound O, which is originally present in ginseng in a trace amount, from a saponin of ginseng, and more specifically to a method capable of obtaining desired target compounds, that is, ginsenoside F2, compound Mc and compound O, in high yields, by treating saponins, obtained from ginseng, with particular enzymes to structurally convert the saponins.

5 Claims, 1 Drawing Sheet

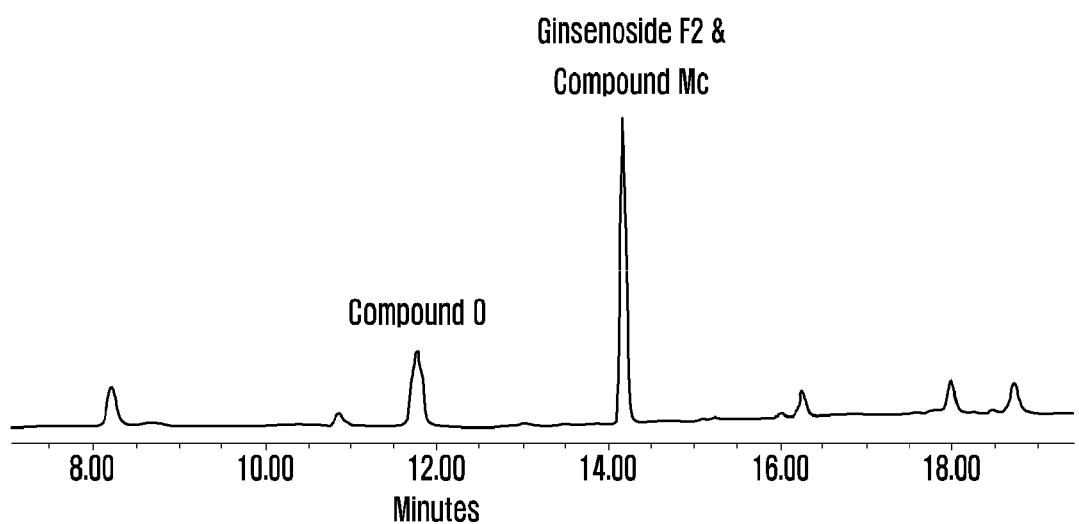

METHOD FOR SELECTIVELY PRODUCING GINSENOSIDE F2, COMPOUND MC OR COMPOUND O FROM SAPONINS OF GINSENG BY ENZYMATIC PROCESS

CROSS REFERENCE TO RELATED APPLICATIONS

This application is a National Stage of International Application No. PCT/KR2016/011900 filed Oct. 21, 2016, claiming priority based on Korean Patent Application No. 10-2015-0147353 filed Oct. 22, 2015.

TECHNICAL FIELD

The present invention relates to a method for selectively producing ginsenoside F2, compound Mc or compound O, which is originally present in ginseng in a trace amount, from saponins of ginseng, and more specifically to a method capable of obtaining desired target compounds, that is, ginsenoside F2, compound Mc and compound O, in high yields, by treating saponins, obtained from ginseng, with particular enzymes to structurally convert the saponins.

BACKGROUND ART

Ginseng saponin has a unique chemical structure different from that of saponin found in other plants. Thus, its pharmacological efficacy is unique, and thus it is also called "ginsenoside" in the sense of ginseng glycoside. Specific types of ginseng saponins include panaxadiol-type ginsenosides Rb1, Rb2, Rc, Rd, compound K, compound Mc, compound O, etc., and panaxatriol-type ginsenosides Re, Rf, Rg1, Rg3, Rg5, Rh1, Rh2, etc., and each of these ginseng saponins exhibit different efficacies.

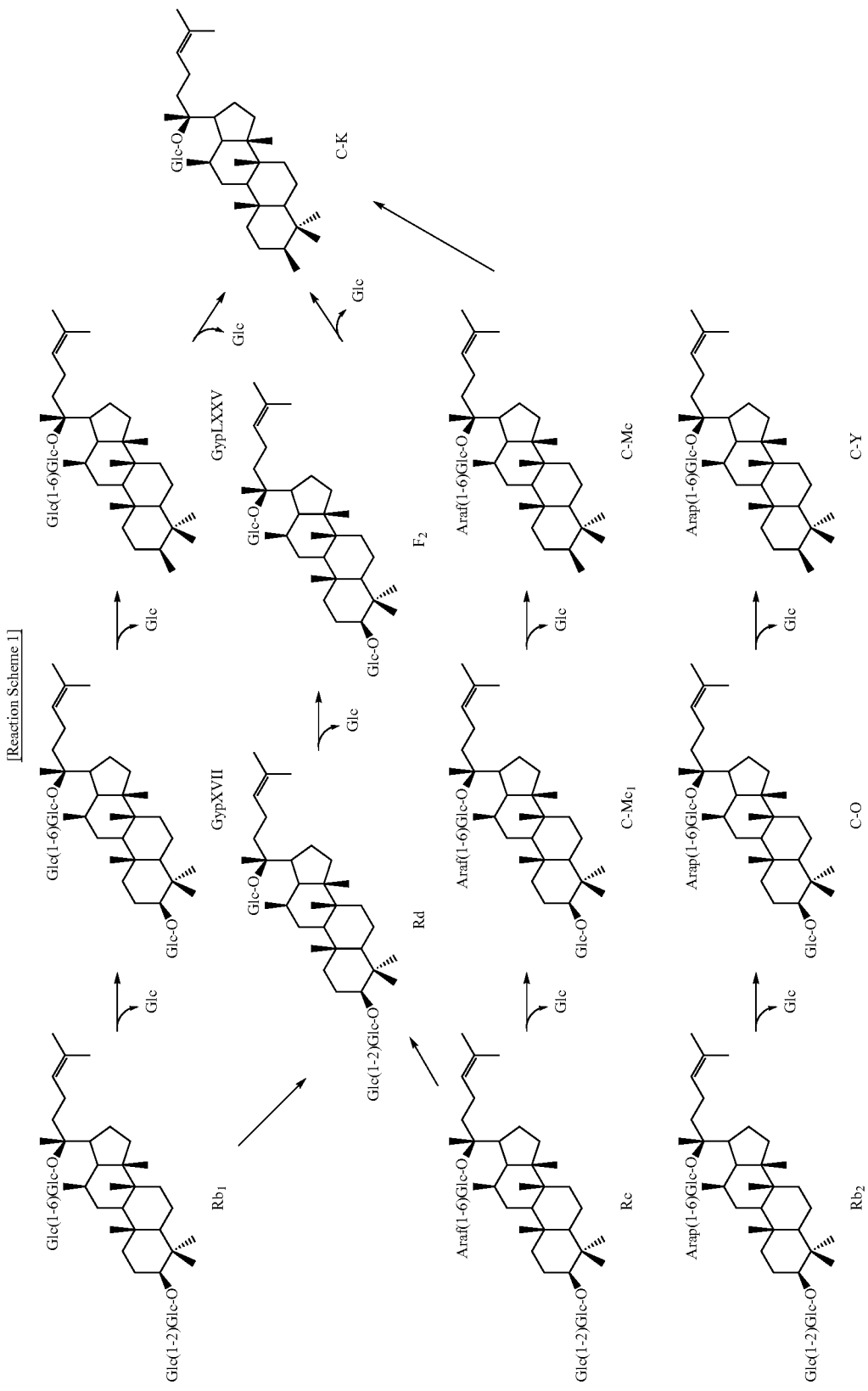
[Reaction Scheme 1]

As shown in the Reaction Scheme 1, particularly, since ginsenosides Rb1, Rb2, Rc, etc., which are panaxadiol type saponins, can be converted into other ginseng saponins by metabolism of microorganisms, a method using enzymes has been used for a long time as a method of converting ginseng saponin into other kinds of specific ginseng saponins.

However, for the conversion reaction using enzymes in the past, non-specificity of enzymes for a substrate is large and thus an extremely large amount of enzyme should be used relative to the saponin substrate used. Further, the enzymatic reaction is not completed with a desired ginseng saponin, but an additional reaction occurs nonspecifically. Thus, since other ginseng saponins were variously produced without being converted only to the desired ginseng saponin, the yield of the desired ginseng saponin was extremely low.

In addition, conventional methods of obtaining ginseng saponins do not convert only to a desired specific ginseng saponin, but provide a technical solution of obtaining various converted ginseng saponins by extraction or the like and then purifying the resultant to isolate only desired ginseng saponins.

However, since these conventional methods require additional cost and time associated with the purification in order to obtain a pure specific ginseng saponin. Therefore, the selling price of ginseng saponins is inevitably increased, and there is a limit to applying a large amount of ginseng saponins to related products.

Furthermore, nonselective removal of sugar in ginsenoside Rb1 can produce ginsenoside Rd, ginsenoside XVII, ginsenoside LXXV, compound K and the like, nonselective removal of sugar in ginsenoside Rb2 can produce compound Y, and nonselective removal of sugar in ginsenoside Rc can produce compound Mc 1. Therefore, if the enzyme reaction occurs nonspecifically, it becomes difficult to obtain metabolites such as ginsenoside F2, compound Mc and the like in high yield.

PRIOR ART LITERATURE

Patent Literature

1. Korean Patent Laid-Open Publication No. 10-2002-0058153 (published on Jul. 12, 2002)

DETAILED DESCRIPTION OF THE INVENTION

Technical Problem

It was expensive to acquire a specific ginseng saponin by a conventional method and also it was difficult to obtain the desired ginseng saponin in large quantities. Therefore, there is a need to develop a production method that can produce a large amount of target ginseng saponins and can save costs.

Accordingly, an object of the present invention is to provide a conversion method of ginseng saponin which can obtain a desired specific ginseng saponin in a high yield and also can be easily carried out Technical Solution In order to achieve the above object, the present invention provides a method for producing ginsenoside F2, compound Mc or compound O by converting saponins of ginseng using at least one selected from the group consisting of pectinase and beta-glucanase isolated from genus *Aspergillus*.

Advantageous Effects

By using the method for converting to ginseng saponins according to the present invention, the desired ginseng saponin can be easily obtained with high yield.

BRIEF DESCRIPTION OF DRAWINGS

FIG. 1 shows the results of confirming ginsenoside F2, compound Mc and compound O produced after the conversion reaction of ginseng saponin though silica gel column chromatography.

DETAILED DESCRIPTION OF THE EMBODIMENTS

The present invention relates to a method for selectively producing ginsenoside F2 (chemical formula 1), compound Mc (chemical formula 2) or compound O (chemical formula 3) by converting saponins of ginseng, particularly a panaxadiol-type saponin, by an enzymatic method. Specifically, through the selective removal of sugar, ginsenoside Rb1 can be converted into ginsenoside F2, ginsenoside Rc can be converted into compound Mc, and ginsenoside Rb2 can be converted into compound O, thereby selectively producing the desired ginseng saponins.

[Chemical Formula 1]

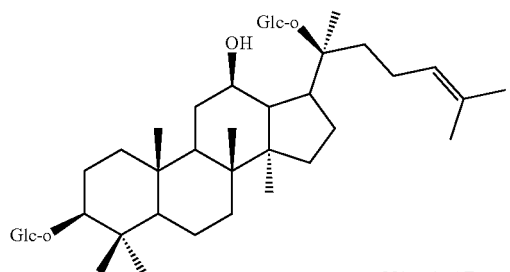

[Chemical Formula 2]

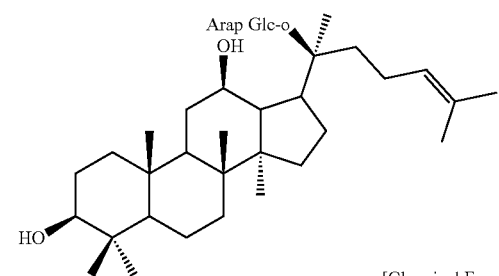

[Chemical Formula 3]

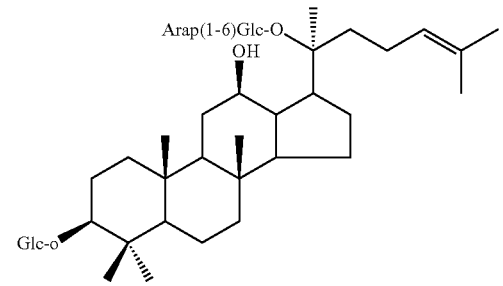

Ginsenoside F2, where Glc is β-D-glucopyranosyl.
Compound Mc where Glc is -β-D-glucopyranosyl and Araf is -α-L-arabinofuranosyl.
Compound O, where Glc is β-D-glucopyranosyl and Arap is α-L-arabinopyranosyl.

According to the method of the present invention, the conversion from saponins of ginseng to a desired ginseng saponin can be efficiently carried out by using enzymes derived from microorganisms, thereby obtaining ginsenoside F2, compound Mc and compound O in high yield.

Specifically, the enzyme used in the present invention is desirably obtained from at least one microorganism selected from the group consisting of the microorganisms belonging to the genus *Aspergillus*, particularly *Aspergillus niger, Aspergillus aculeatus, Aspergillus luchuensis* and *Aspergillus oryzae*, and those obtained from *Aspergillus aculeatus* are most preferred.

In addition, the enzyme used in the present invention may be lactase, cellulase, beta-galactosidase, naringinase, hemicellulase, beta-glucanase, pectinase, or a mixture thereof, isolated from a microorganism of the genus *Aspergillus*, and pectinase, beta-glucanase, or a mixture thereof are preferred.

Even the same type of enzyme that performs mostly the same function, the site where the enzyme functions specifically in the substrate varies depending on the species of the microorganism from which the enzyme is derived, resulting in a difference in substrate specificity. Therefore, in the present invention, it is most desirable to use at least one selected from the group consisting of pectinase and beta-glucanase obtained from *Aspergillus aculeatus*.

In the present invention, saponin of ginseng is dissolved in a solvent in an amount of 0.01 to 20% by weight, and then the saponin is converted into the desired ginseng saponin by an enzymatic method using the above-mentioned enzymes. The solvents used here are preferably those that do not inhibit the activity of enzymes, for example, an aqueous solvent such as water or a buffer solution, or a mixture of an aqueous solvent and an organic solvent such as water or a buffer solution can be used. Specifically, the buffer solution used here may be acetic acid, citric acid, phosphoric acid, citric acid-phosphoric acid, or the like, and the organic solvent may be acetonitrile, dioxane, dimethyl sulfoxide, methanol, ethanol, 1-propanol, 2-propanol, or the like. The pH range of the solvent that can be used is preferably 2.5 to 7.5, more preferably 3 to 6, still more preferably 3.5 to 5.5.

In the method of the present invention, the enzyme to be used is added in an amount of preferably 1 to 500% by weight, more preferably 10 to 400% by weight, still more preferably 10 to 200% by weight, based on the amount of the substrate used.

The reaction temperature must be a temperature condition under which no enzyme inactivation occur, but the temperature is maintained in the range of preferably 30 to 60° C., more preferably 35 to 60° C., still more preferably 40 to 55° C.

Furthermore, the reaction time is not particularly limited as long as it is a period during which the activity of the enzyme is maintained, but it is desirable to perform the reaction while stirring for 1 to 120 hours, preferably 1 to 96 hours, more preferably 24 to 96 hours, still more preferably 24 to 72 hours.

Subsequently, a reaction solution containing a large amount of ginsenoside F2, compound Mc and compound O can be obtained by inactivating the enzyme using a known method such as heating in a boiling water bath.

DETAILED DESCRIPTION OF THE EMBODIMENTS

Hereinafter, the present invention will be described in detail by way of Examples. However, these Examples are given for illustrative purposes only, and are not intended to limit the scope of the invention thereto.

[Reference Example 1] Production of Ginseng Purified Saponin 20 l of ethanol was added to 2 kg of red ginseng, white ginseng, fresh ginseng, tiny-sized ginseng or leaves, flowers and fruits of ginseng, and extracted three times under reflux and then immersed at 15° C. for 6 days. Thereafter, the residue and the filtrate were isolated through filter cloth-filtration and centrifugation, and the isolated filtrate was concentrated under reduced pressure. The extract obtained was suspended in water, and then extracted five times with 1 l of ether to remove a pigment. The aqueous layer was extracted three times with 1 l of 1-butanol. The total 1-butanol layer thus obtained was treated with 5% KOH, washed with distilled water and then concentrated under reduced pressure to obtain 1-butanol extract, which was dissolved in a small amount of methanol, and then added to a large amount of ethyl acetate. The resulting precipitate was dried to thereby obtain 40 to 80 g of ginseng purified saponin (including ginsenoside Rb1, Rb2, Rc, Rd, Re, Rg1, Rf, etc.).

[Example 1] Production of Ginsenoside F2, Compound Mc and Compound O Through Enzymatic Reaction 10 g of ginseng purified saponin (including ginsenoside Rb1, Rb2, Rc, Rd, Re, Rg1, Rf, etc.) of the Reference Example 1 was dissolved in 1 l of water.

Thereafter, pectinase isolated from *Aspergillus aculeatus* was added to the above mixed solution in an amount of 200% by weight relative to the substrate, and the mixture was reacted at 30° C. for 24 hours. When the substrate was completely disappeared by periodic confirmation by thin layer chromatography, the enzyme was inactivated by heating in a boiling water bath for 10 minutes, thereby completing the reaction. Finally, ethyl acetate was added to the reaction solution at a ratio of 1:1 (ratio of volume to the reaction solution), extracted three times, concentrated and then subjected to silica gel column chromatography (chloroform:methanol=9:1) to isolate ginsenoside F2, compound Mc and compound O (FIG. 1).

2.66 g of ginsenoside Rb1, 0.73 g of ginsenoside Rb2, 1.23 g of ginsenoside Rc and 0.38 g of ginsenoside Rd were present in 10 g of the ginseng saponin of Reference example 1 used. Ginsenoside F2 was converted from ginsenoside Rb1 and ginsenoside Rd in a yield of 95% or more, compound Mc was converted from ginsenoside Rc in a yield of 95% or more, compound O was converted from ginsenoside Rb2 in a yield of 95% or more.

The invention claimed is:

1. A method for producing ginsenoside F2 of the following Chemical Formula 1, compound Mc of the following Chemical Formula 2 or compound O of the following Chemical formula 3, from saponins of ginseng by enzyme conversion, Chemical Formula 1

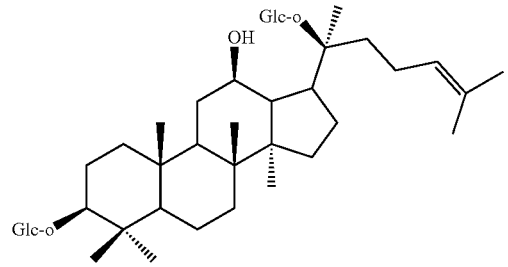

Ginsenoside F2, wherein Glc is β-D-glucopyranosyl;

Chemical Formula 2

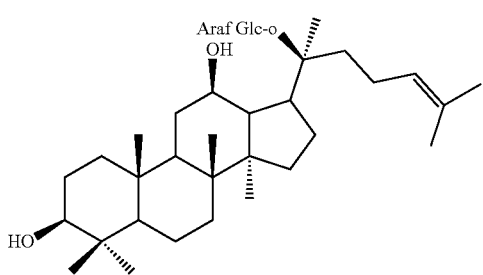

Compound Mc wherein, Glc is β-D-glucopyranosyl and Araf is α-L-arabinofuranosyl;

Chemical formula 3

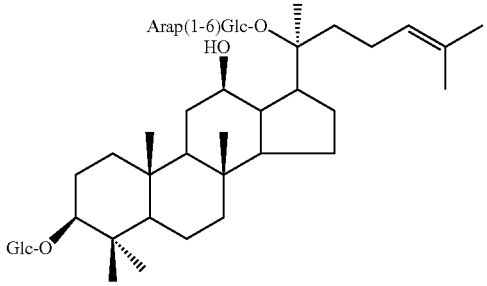

Compound O, wherein, Glc is β-D-glucopyranosyl and Arap is α-L-arabinopyranosyl;

wherein the method comprises the steps of:
1) dissolving the saponins of ginseng as a substrate in an aqueous solvent or a mixed solution of an aqueous solvent and an organic solvent' adding thereto an enzyme, and performing the reaction at a temperature of 30 to 60° C. for 24 to 96 hours with stirring in a heated water bath, wherein the solvent has a pH in the range of 3 to 6, wherein the saponins of ginseng comprise ginsenosides Rb1, Rb2, Rc and Rd, and wherein the enzyme is added In an amount of 10 to 400% by weight based on the amount of the substrate;
wherein the enzyme is pectinase obtained from *Aspergillus aculeatus;*
2) inactivating the pectinase when the substrate is disappeared, thereby completing the reaction; and
3) adding ethyl acetate to a reaction solution obtained in step 2), followed by extraction and concentration, thereby isolating ginsenoside F2, compound Mc or compound O.

2. The method according to claim 1, wherein the enzyme is added in an amount of 200% by weight based on the amount of the substrate.

3. The method according to claim 1, wherein the reaction is performed at a temperature of 30° C.

4. The method according to claim 1, wherein the reaction is performed for 24 hours.

5. The method according to claim 1, wherein the solvent has a pH in the range of 3.5 to 5.5.

* * * * *